US00PP17917P2

(12) United States Plant Patent
Vlielander

(10) Patent No.: US PP17,917 P2
(45) Date of Patent: Aug. 14, 2007

(54) ***KALANCHOE* PLANT NAMED 'FIVERANDA LIGHT PINK'**

(50) Latin Name: ***Kalanchoe guignardii*×*Kalanchoe blossfeldiana***
Varietal Denomination: Fiveranda Light Pink

(75) Inventor: Ike Vlielander, De Lier (NL)

(73) Assignee: Fides B.V., De Lier (NL)

( * ) Notice: Subject to any disclaimer, the term of this patent is extended or adjusted under 35 U.S.C. 154(b) by 5 days.

(21) Appl. No.: 11/290,155

(22) Filed: Nov. 30, 2005

(51) Int. Cl.
*A01H 5/00* (2006.01)

(52) U.S. Cl. ..... Plt./339
(58) Field of Classification Search ..... Plt./339, Plt./335
See application file for complete search history.

*Primary Examiner*—Anne Marie Grunberg
*Assistant Examiner*—S. B. McCormick-Ewoldt

(57) ABSTRACT

A new cultivar of *Kalanchoe* plant named 'Fiveranda Light Pink' that is characterized by light pink flowers, vigorous growth, strong branching, long flower life, short response time and a uniform crop.

1 Drawing Sheet

Botanical classification: *Kalanchoe guignardii*×*Kalanchoe blossfeldiana.*
Variety denomination: 'Fiveranda Light Pink'.

BACKGROUND OF THE INVENTION

The present invention relates to a new and distinct cultivar of *Kalanchoe* plant botanically known as *Kalanchoe guignardii*×*Kalanchoe blossfeldiana* and hereinafter referred to by the cultivar name 'Fiveranda Light Pink'.

The new cultivar is the product of a breeding program conducted by the inventor in a cultivated area of De Lier, The Netherlands. The objective of the breeding program is to develop new *Kalanchoe* cultivars with interesting and unique flower colors and shapes.

'Fiveranda Light Pink' is a hybrid that originated from the induced hybridization of the female or seed parent *Kalanchoe guignardii* (not patented) and the male or pollen parent *Kalanchoe blossfeldiana* 'Petero' (U.S. Plant Pat. No. 12,155). The cultivar 'Fiveranda Light Pink' was selected by the inventor in 1999 as a single plant within the progeny of the stated cross in a controlled environment of De Lier, The Netherlands.

Asexual reproduction first occurred when terminal cuttings of the new cultivar 'Fiveranda Light Pink' were propagated in 2000 in De Lier, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Kalanchoe* cultivar 'Fiveranda Light Pink'. These traits in combination distinguish 'Fiveranda Light Pink' as a new and distinct cultivar apart from other existing known varieties of *Kalanchoe.*

1. *Kalanchoe* 'Fiveranda Light Pink' exhibits vigorous growth.
2. *Kalanchoe* 'Fiveranda Light Pink' exhibits strong branching.

3. *Kalanchoe* 'Fiveranda Light Pink' exhibits a long flower life.
4. *Kalanchoe* 'Fiveranda Light Pink' exhibits a short response time.
5. *Kalanchoe* 'Fiveranda Light Pink' exhibits light pink flowers.
6. *Kalanchoe* 'Fiveranda Light Pink' exhibits a uniform crop.

The new cultivar 'Fiveranda Light Pink' is distinguishable from the female parent *Kalanchoe guignardii* by the following characteristics:

1. 'Fiveranda Light Pink' exhibits more vigorous growth than *Kalanchoe guignardii.*
2. 'Fiveranda Light Pink' exhibits lighter pink flowers than the female parent *Kalanchoe guignardii.*
3. 'Fiveranda Light Pink' exhibits flowers that open more fully than *Kalanchoe guignardii.*

The new cultivar 'Fiveranda Light Pink' is distinguishable from the male parent *Kalanchoe* 'Petero' by the following characteristics:

1. 'Fiveranda Light Pink' is larger than 'Petero'.
2. 'Fiveranda Light Pink' exhibits light pink flowers. The flowers of 'Petero' are lighter pink in color.
3. 'Fiveranda Light Pink' exhibits stronger branching.

The closest comparison cultivar is *Kalanchoe* 'Fiveranda Pink' (U.S. Plant Pat. No. 16,189). The new cultivar 'Fiveranda Light Pink' is distinguishable from 'Fiveranda Pink' by the following characteristics:

1. 'Fiveranda Light Pink' exhibits light pink flowers. The flowers of 'Fiveranda Pink' are darker pink.

BRIEF DESCRIPTION OF THE DRAWING

The accompanying photograph illustrates the distinguishing traits of *Kalanchoe* 'Fiveranda Light Pink'. The plant in the photograph shows an overall view of a 18 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Kalanchoe* cultivar named 'Fiveranda Light Pink'. Data was collected in De Lier, The Netherlands from 18 week glass greenhouse grown plants in 6 inch diameter containers. The time of year was Spring and the temperature was kept at 20° Centigrade during the day and night. The light level was natural outdoor light supplemented with artificial light below 10,000 lux. Photoperiodic treatments of 3 weeks of long days (more than 14 hours of light) followed by 8 weeks of short days (more than 14 hours of darkness) were used. No overhead watering was applied during the last 6 weeks. Color determinations are in accordance with The Royal Horticultural Society Colour Chart 2001 edition, except where general color terms of ordinary dictionary significance are used. The growing requirements are similar to the species. 'Fiveranda Light Pink' has not been tested under all possible conditions and phenotypic differences may be observed with variations in environmental, climatic, and cultural conditions, however, without any variance in genotype.

Botanical classification: *Kalanchoe* 'Fiveranda Light Pink'.
Use: Ornamental Annual.
Parentage: 'Fiveranda Light Pink' is a hybrid plant that resulted from the induced hybridization of the following parent plants:
- *Female parent.*—*Kalanchoe guignardii.*
- *Male parent.*—*Kalanchoe blossfeldiana* 'Petero'.

Vigor: Very Strong.
Growth habit: Upright and uniform.
Plant shape: Rounded, Triangular.
Suitable container size: 6 inch diameter container.
Height: 29 cm. in height.
Width: 38 cm. in width.
Low temperature tolerance: 15 degrees Centigrade.
High temperature tolerance: 35 degrees Centigrade.
Propagation: Terminal cuttings.
Time to initiate roots: 10-14 days to initiate roots at 21 degrees Centigrade.
Time to produce a rooted cutting or liner: 15-18 days at 21 degrees Centigrade.
Crop time: 11-14 weeks are required to produce a finished flowering plant.
Root system: Fine and fibrous.
Stem:
- *Branching habit.*—Freely branching with shoots at every node.
- *Average number of lateral branches:* 10-12.
- *Pinching.*—Not Required.
- *Lateral branch diameter.*—9-12 mm. in diameter.
- *Lateral branch length.*—17-22 cm. in length.
- *Lateral branch strength.*—Very strong.
- *Stem diameter.*—18-22 mm. in diameter.
- *Stem color.*—147A.
- *Stem shape.*—Straight.
- *Pubescence.*—Absent.
- *Internode length.*—3-5 cm. between nodes.
- *Aspect.*—Upright.

Foliage:
- *Texture.*—Both sides glabrous, coriaceous, succulent.
- *Leaf arrangement.*—Opposite.
- *Compound or single.*—Single.
- *Quantity of leaves per lateral branch.*—8-13.
- *Leaf shape.*—Ovate/Elliptic.
- *Leaf apex.*—Acute to Obtuse.
- *Leaf base.*—Acute.
- *Leaf length.*—17 cm. in length.
- *Leaf width.*—12 cm. in width.
- *Pubescence.*—Absent.
- *Leaf margin.*—Crenate.
- *Young leaf color* (*lower surface*).—147B.
- *Young leaf color* (*upper surface*).—147A.
- *Mature leaf color* (*lower surface*).—147B.
- *Mature leaf color* (*upper surface*).—147A.
- *Vein color* (*lower surface*).—147B.
- *Vein color* (*upper surface*).—147A to 147B.
- *Venation pattern.*—Pinnate.
- *Leaf attachment.*—Petiolate.
- *Petiole dimensions.*—20 mm. in length and 6-8 mm. in width.
- *Petiole color upper side.*—147A to 147B.
- *Petiole color lower side.*—147A to 147B.

Flower:
- *Inflorescence arrangement.*—Single flowers arranged in racemes forming an umbel.
- *Flowering habit.*—Continuous.
- *Quantity of flowers per lateral stem.*—Over 40.
- *Quantity of flowers buds per lateral stem.*—Over 40.
- *Quantity of flowers and buds per plant.*—Over 250.
- *Natural flowering season.*—November/December in the Northern Hemisphere.
- *Time to flower.*—10-12 weeks.
- *Fragrance.*—None.
- *Flower bud length.*—10 mm. in length.
- *Flower bud diameter.*—2 mm. in diameter.
- *Flower bud shape.*—Oblong, tubular and ovoid.
- *Bud color.*—55C to 55D.
- *Rate of bud opening.*—1 day.
- *Flower aspect.*—Cupped/Raceme/Bell.
- *Flower shape.*—Petals fused at base to form a bell shaped corolla.
- *Flower dimensions.*—16 mm. in diameter and 14 mm. in height.
- *Flower longevity.*—Approximately 20 days.
- *Petal appearance.*—Shiny.
- *Petal texture.*—Glabrous.
- *Number of petals.*—4.
- *Fused or unfused.*—Unfused.
- *Petal appearance.*—Flat to partially upright.
- *Petal shape.*—Ovate.
- *Petal margin.*—Entire.
- *Petal apex.*—Obtuse.
- *Petal dimensions.*—7 mm. in length and 4 mm. in width.
- *Petal color when opening* (*upper side*).—65A to 65B.
- *Petal color when opening* (*under side*).—65C.
- *Petal color fully opened* (*upper side*).—65A to 65B.
- *Petal color fully opened* (*under side*).—65C.
- *Petal color fading to.*—65B to 65C.
- *Self-cleaning or persistent.*—Persistent.

Sepals:
- *Number of sepals.*—Four.
- *Sepal aspect.*—Upright, rigid.
- *Sepal shape.*—Oblong/Pointed.
- *Sepal margin.*—Entire.
- *Sepal apex.*—Acute.
- *Sepal base.*—Rounded.
- *Sepal surface.*—Smooth, shiny.
- *Sepal dimensions.*—6 mm in length and 2 mm. in width.

*Sepal color* (*upper side*).—138D.
*Sepal color* (*under side*).—138D.

Calyx:
*Calyx shape.*—Funnel.
*Calyx dimensions.*—16 mm in length and 4 mm in diameter.

Peduncle:
*Peduncle dimensions.*—7 mm. in length and 1 mm. in diameter.
*Peduncle aspect.*—Rigid.
*Peduncle texture.*—Smooth.
*Peduncle color.*—138B.
*Peduncle strength.*—Strong.

Reproductive organs:
*Stamen number.*—8.
*Anther shape.*—Flat, Elliptic.
*Anther dimensions.*—0.3 mm. in length and 0.3 mm. in width.
*Anther color.*—150D.
*Amount of pollen.*—Low.
*Pollen color.*—12A.
*Pistil number.*—4.
*Pistil dimensions.*—1 mm. in length.
*Stigma shape.*—Flat.
*Stigma color.*—8D.
*Style length.*—10 mm.
*Style color.*—138D.
*Ovary color.*—138D.

Seed:
*Seed length.*—0.1 mm.
*Seed diameter.*—0.05 mm.
*Seed color.*—166C.
*Quantity of seeds.*—0-500 per plant.

Disease and insect resistance: No disease problems observed, slight susceptibility to aphids.

What is claimed is:

1. A new and distinct variety of *Kalanchoe* plant named 'Fiveranda Light Pink' as described and illustrated.

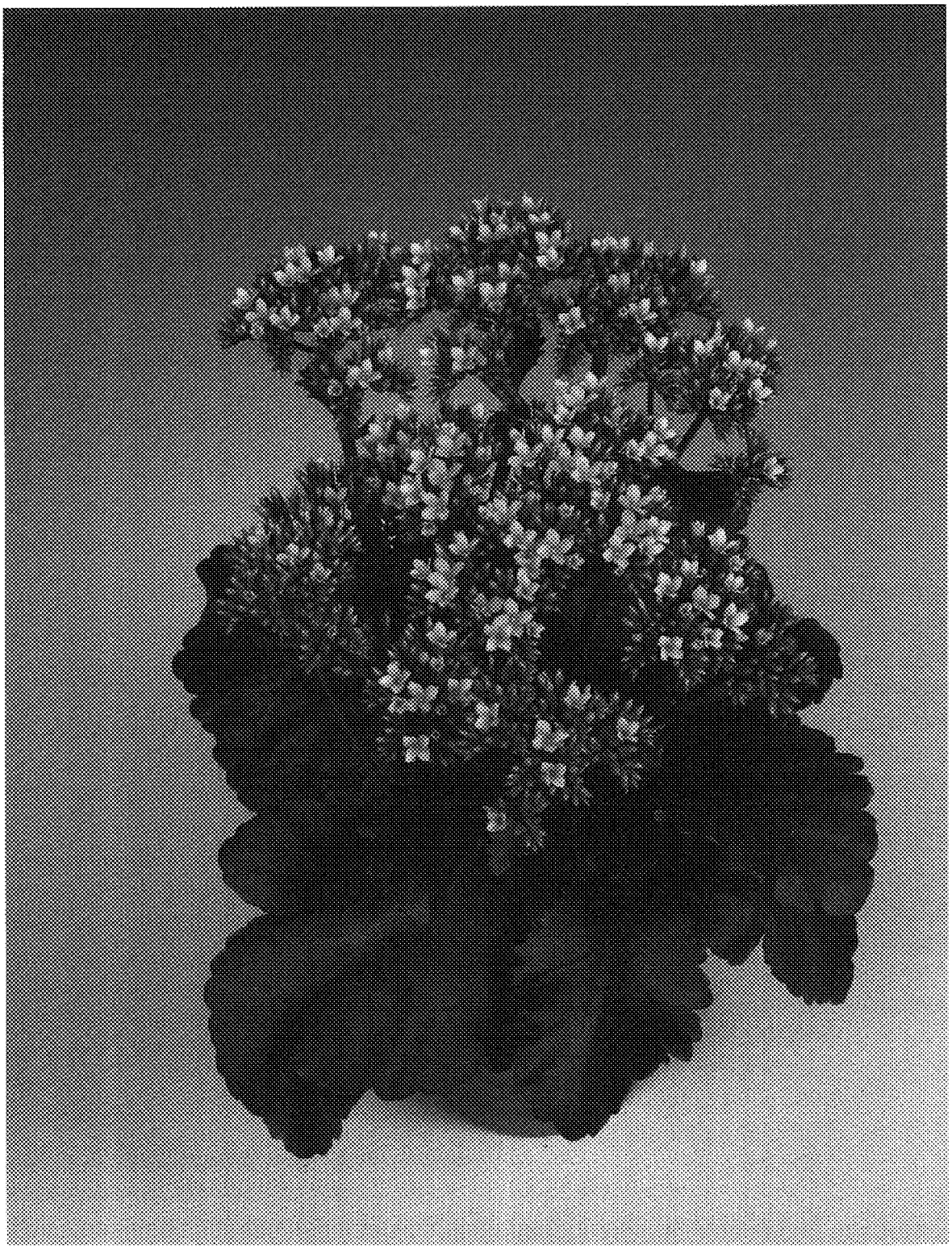

* * * * *